(12) United States Patent
Saint Martin

(10) Patent No.: US 7,686,834 B2
(45) Date of Patent: Mar. 30, 2010

(54) ANCHORING MEMBER WITH SAFETY RING

(75) Inventor: Pierre Henri Saint Martin, Merignac (FR)

(73) Assignee: Stryker Spine (FR)

( * ) Notice: Subject to any disclaimer, the term of this patent is extended or adjusted under 35 U.S.C. 154(b) by 1292 days.

(21) Appl. No.: 10/096,991

(22) Filed: Mar. 13, 2002

(65) Prior Publication Data

US 2002/0133154 A1 Sep. 19, 2002

(30) Foreign Application Priority Data

Mar. 15, 2001 (FR) .................................. 01 03515

(51) Int. Cl.
*A61B 17/70* (2006.01)
(52) U.S. Cl. ........................ 606/264; 606/266; 606/270
(58) Field of Classification Search ................... 606/61,
606/60, 53, 54, 71, 70, 72, 73, 270, 266,
606/264, 246, 279
See application file for complete search history.

(56) References Cited

U.S. PATENT DOCUMENTS

| | | | |
|---|---|---|---|
| 5,466,237 A | | 11/1995 | Byrd, III et al. |
| 5,690,630 A | * | 11/1997 | Errico et al. .................... 606/61 |
| 5,879,350 A | * | 3/1999 | Sherman et al. ................ 606/61 |
| 5,885,286 A | * | 3/1999 | Sherman et al. ................ 606/61 |
| 5,891,145 A | * | 4/1999 | Morrison et al. ............... 606/61 |
| 6,010,503 A | | 1/2000 | Richelsoph et al. |
| 6,053,917 A | * | 4/2000 | Sherman et al. ................ 606/61 |
| 6,074,391 A | * | 6/2000 | Metz-Stavenhagen et al. . 606/61 |
| 6,090,111 A | * | 7/2000 | Nichols ........................ 606/61 |
| 6,280,442 B1 | * | 8/2001 | Barker et al. ................... 606/60 |
| 6,331,179 B1 | * | 12/2001 | Freid et al. ..................... 606/61 |
| 6,402,752 B2 | * | 6/2002 | Schaffler-Wachter et al. .. 606/61 |
| 6,471,705 B1 | * | 10/2002 | Biedermann et al. .......... 606/61 |
| 6,488,681 B2 | * | 12/2002 | Martin et al. .................. 606/61 |
| 6,565,565 B1 | * | 5/2003 | Yuan et al. ..................... 606/61 |
| 6,869,433 B2 | * | 3/2005 | Glascott ....................... 606/73 |

FOREIGN PATENT DOCUMENTS

| | | | |
|---|---|---|---|
| DE | 299 03 342 U1 | 6/1999 | |
| DE | 29903342 | * 9/1999 | .................. 606/246 |
| EP | 0 613 664 B1 | 4/2001 | |
| JP | 6-296621 | 10/1994 | |
| JP | 7-59795 | 3/1995 | |
| JP | 8-257035 | 10/1996 | |
| JP | 11-318933 | 11/1999 | |
| WO | WO-96/12976 A1 | 5/1996 | |
| WO | 98/27884 | 7/1998 | |
| WO | WO-99/65415 | 12/1999 | |
| WO | WO 01 15612 A1 | 3/2000 | |

OTHER PUBLICATIONS

French Preliminary Search Report dated Nov. 27, 2001.

* cited by examiner

*Primary Examiner*—Pedro Philogene
(74) *Attorney, Agent, or Firm*—Lerner, David, Littenberg, Krumholz & Mentlik, LLP

(57) ABSTRACT

A spinal osteosynthesis assembly comprises a connector, a bone anchor capable of being received in the connector, a connecting member capable of being received in the connector, and a ring capable of coming into contact with the bone anchor, the connecting member being able to come to bear against the ring and the bone anchor when the ring and the bone anchor are fitted in the connector.

23 Claims, 4 Drawing Sheets

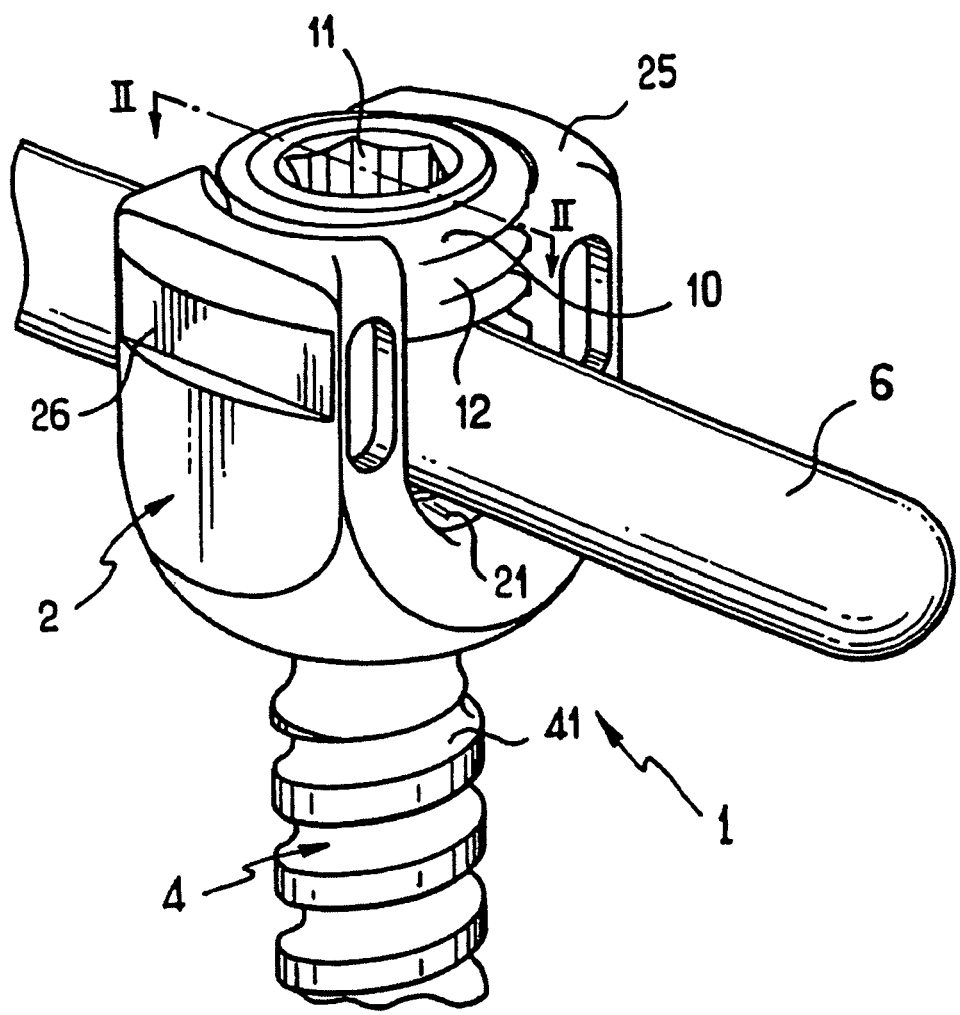
FIG_1
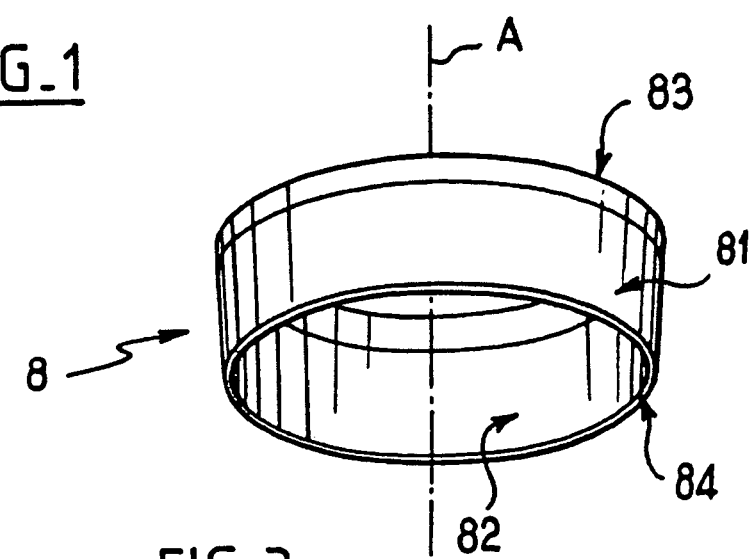
FIG_3

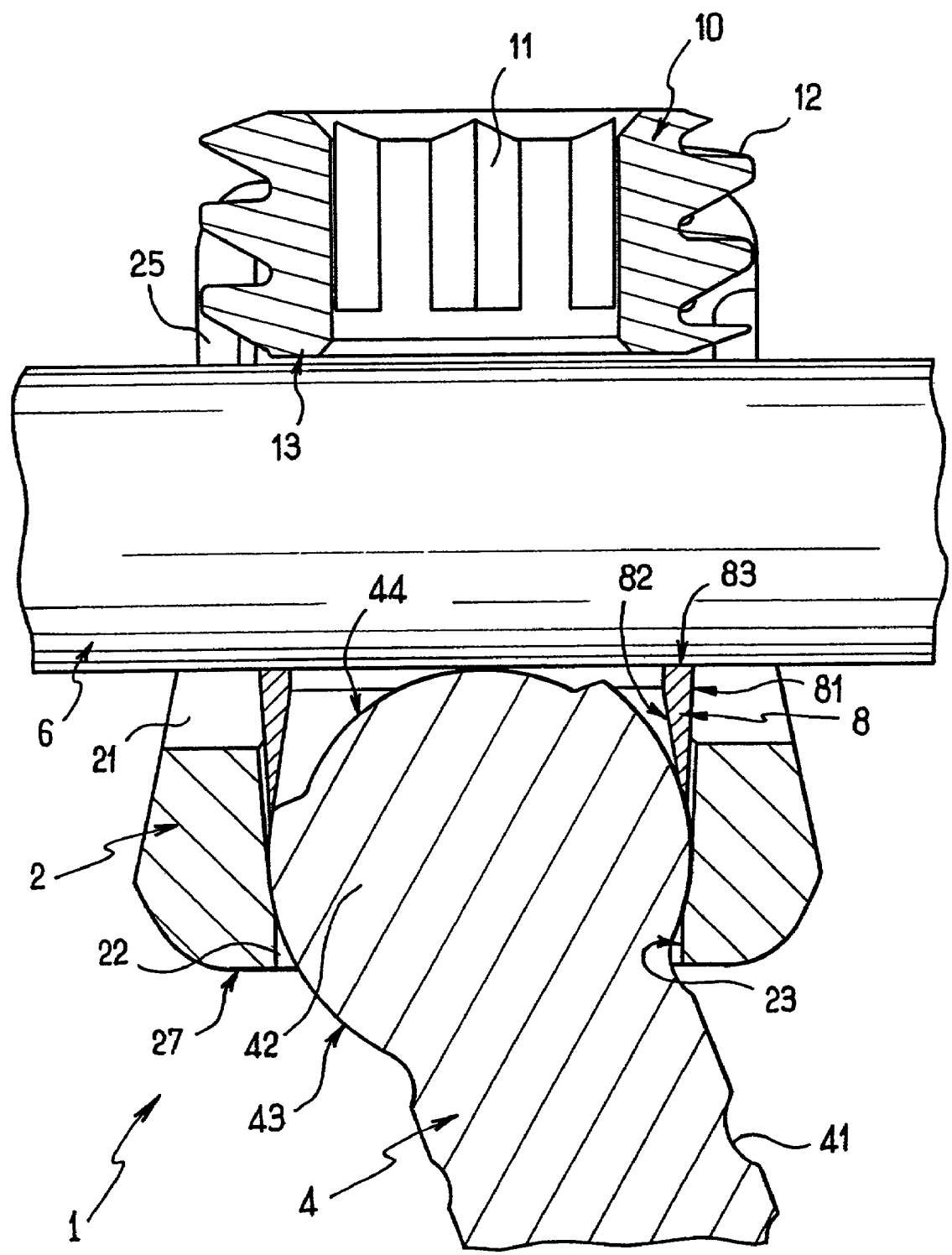
FIG_2

ANCHORING MEMBER WITH SAFETY RING

The invention relates to osteosynthesis systems particularly for surgery on the spinal column.

Document WO 98/12 976 discloses a spinal osteosynthesis system comprising an anchoring member of the polyaxial screw type which is immobilized in position by the link rod bearing against a crown, the rounded lower surface of which bears in a complementary manner on the spherical head of the bone screw lodged in the bottom of a housing made in a connector. Such a system involves a very high bearing force between the rod and the crown in order that the pressure per unit area between the crown and the screw head is high enough to prevent any movement of one with respect to the other, which movement would have the effect of creating instability that is detrimental to the desired osteosynthesis.

One object of the invention is to provide a position-locking device which is more reliable for the same clamping force.

To do that, an aspect of the invention provides a spinal osteosynthesis assembly comprising a connector, bone anchoring means capable of being received in the connector, a connecting member capable of being received in the connector, and a ring capable of coming into contact with the head, the connecting member being able to come to bear simultaneously against the ring and the head when the ring and the anchoring means are fitted in the connector.

Thus, when locking the osteosynthesis system, the bearing of the connecting member on the ring forces the latter to come to bear against the anchoring means to immobilize the anchoring means in position within the connector, and the simultaneous bearing of the connecting member on the anchoring means enhances the previous immobilization, making it more secure while at the same time maintaining the same clamping force for locking.

Advantageously, the ring has at least one conical face.

Advantageously, the ring has a face able to come into contact with the anchoring means.

Advantageously, the ring has a face able to come into contact with a wall of the connector.

Advantageously, the faces are coaxial.

Advantageously, the ring has a flat upper edge perpendicular to an axis of the ring and able to come into contact with the connecting member.

Advantageously, the ring has a flat lower edge perpendicular to an axis of the ring.

Advantageously, the ring is able to extend between the wall and the anchoring means when the connecting member bears as mentioned.

Advantageously, the ring is deformed when the connecting member bears as mentioned, with reference to the shape that the ring had before fitting.

Advantageously, the ring has a wall thickness which varies according to a height.

Thus, the ring has a cross section in the shape of a wedge which, when the system is locked, simply wedges between the wall of the connector and the anchoring means and this, in a simple way, will further enhance the positional immobilization.

Advantageously, the ring comprises a slot.

Advantageously, the slot is arranged in such a way that the ring forms a non-closed annulus.

Advantageously, the ring comprises a number of slots distributed uniformly about a circumference of the ring.

Advantageously, the anchoring means comprise a head having a roughly spherical face.

Advantageously, the head has a first spherical face and a second spherical face which have the same center and significantly different diameters.

Advantageously, the anchoring means form a polyaxial screw.

Advantageously, the assembly comprises a locking member able to come to bear against the connecting member.

Also provided according to the invention is an osteosynthesis system comprising an assembly exhibiting at least one of the abovementioned features.

Other features and advantages of the invention will become apparent during the following description of a preferred embodiment. In the appended drawings:

FIG. 1 is a perspective view of the preferred embodiment of the invention;

FIG. 2 is a view in section on II-II of the embodiment of FIG. 1;

FIG. 3 is a perspective view of the ring of the preferred embodiment;

Figure 4:
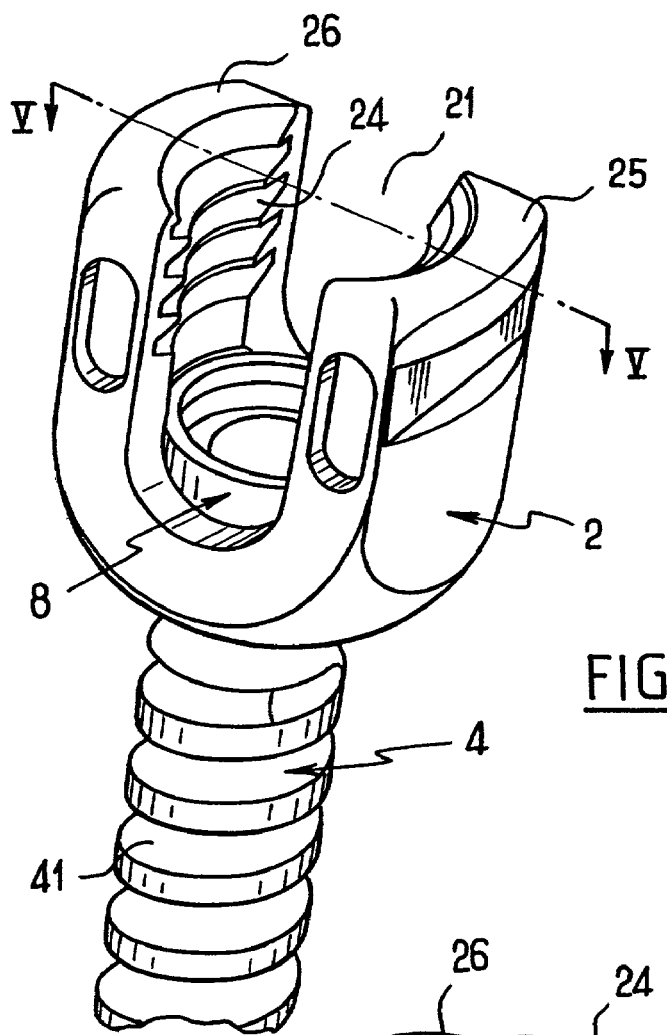
FIG. 4 is a perspective view of the embodiment of FIG. 1 prior to the fitting of the connecting member.

A preferred embodiment will be described with reference to the various FIGS. 1 to 5. The assembly for osteosynthesis of the spinal column 1 here comprises a connector 2, a connecting member 6 and anchoring means 4. Here, the connecting member 6 is an osteosynthesis rod and the anchoring means 4 are formed by a pedicle screw. The assembly 1 also comprises a ring 8 and a locking member 10 capable of locking the assembly 1 in position.

The connector 2 comprises a U-shaped opening 21 forming the upper part of the connector 2. This U-shaped opening 21 is delimited by two branches 25 and 26 which extend roughly parallel with respect to each other. The internal faces of the branches 25 and 26 which extend facing each other comprise a screw thread 24. Furthermore, the connector 2 in its lower part comprises an internal housing 22 having a wall 23. The upper part of the internal housing 22 opens into the bottom of the U-shaped opening 21 and the lower part of the internal housing 22 opens onto a lower face 27 of the connector 2. On the same side as the lower face 27, the wall 23 has a conical section designed so that the opening at the lower face 27 is smaller than the opening at the bottom of the U-shaped opening 21.

The locking member 10 comprises operating means 11 which here are in the form of a through-orifice 11 with a hexagonal socket. This hexagonal socket is designed to accommodate a hexagonal bit fitted to a screwdriver for operating it. Furthermore, the locking member 10 comprises, on its external side wall, a screw thread 12 that complements the screw thread 24 of the connector 2 between the branches 25 and 26 of which it is able to be received.

The anchoring means 4 are here in the form of a pedicle screw comprising an anchoring part 41 exhibiting a bone thread, surmounted by a head 42 which here is roughly spherical. The head 42 has a first spherical surface 43 and, forming the top, a second spherical surface 44, the diameter of which is smaller than the diameter of the spherical surface 43 but has the same center thereas.

Similar osteosynthesis systems can be found in document EP-0 613 664.

The ring 8 is of annular shape and has a first face 82 delimiting the internal wall of the ring, a second face 81 delimiting the external wall of the ring and upper 83 and lower 84 edges perpendicular to the geometric axis of revolution A of the ring 8. The faces 81 and 82 are coaxial and preferably of conical shape. Their respective generators are not mutually parallel. Thus, the faces are arranged one with respect to the other in such a way that the thickness of the ring 2 at the upper edge 83 is greater than the thickness of the ring 8 at the lower edge 84. The cross section of the ring thus has a wedge shape, giving the ring 8 a tapered shape. However, one of the generators of the faces 81 and 82 may be roughly parallel to the axis of revolution A.

Figure 5:
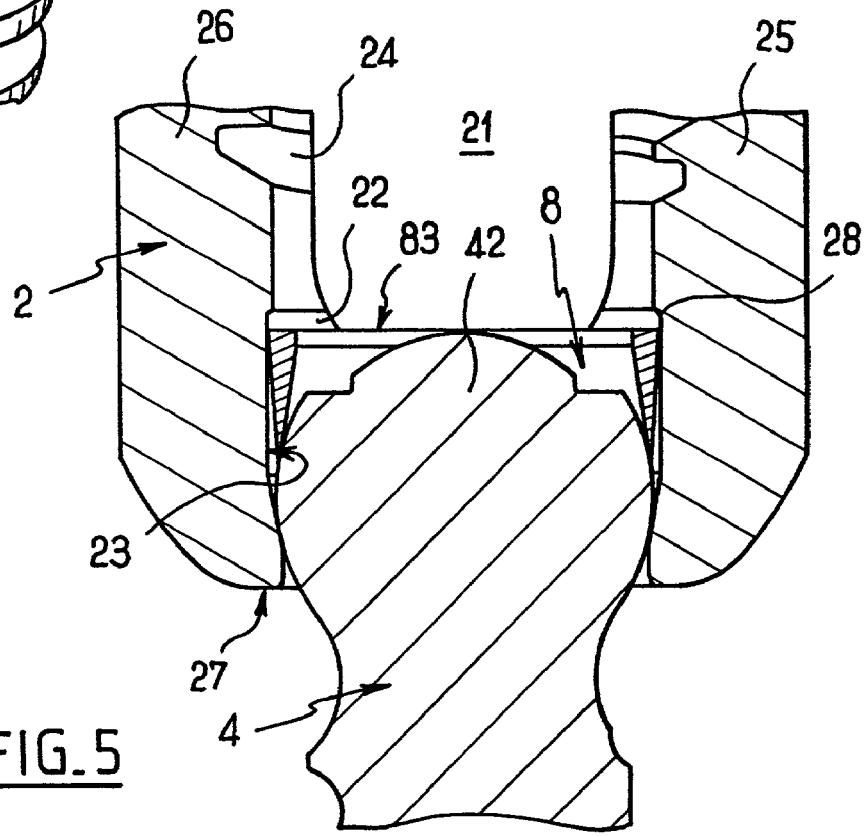
FIG. 5 is a view in section on V-V of the embodiment of FIG. 4.

Prior to use by a surgeon, the connector 2, the anchoring means 4 and the ring 8 are fitted together. More particularly, the head 42 of the anchoring means is inserted into the internal housing 22 of the connector 2. The ring 8 is then itself inserted into the internal housing 22 of the connector 2. Thus, the head 42 of the anchoring means 4 finds itself held captive in the internal housing 22 against exiting upward by the presence, inside the internal housing 22, of the ring 8, which is itself held captive, as will be seen later on. The head 42 is retained against exiting downward by the presence of the conical section of the wall 23 of the internal housing 22, which has an opening at the lower face 27 of the connector 2, the dimensions of which are smaller than the diameter of the surface 43 of the head 42. In addition, the ring 8 is held captive by retaining means 28 present within the internal housing 22. Here, the retaining means 28 stem from the difference in size between the internal housing 22 and the U-shaped opening 21, this difference forming a rim against which the upper edge 83 of the ring 8 abuts from below. This assembly is illustrated in FIGS. 4 and 5.

In use during a surgical operation, the surgeon fits an assembly as described above into the pedicle. He then fits the connecting member 6, inserting it into the U-shaped opening 21 of the connector 2. He then fits the locking member 10 between the branches 25 and 26, engaging the screw thread 12 of the locking member 10 with the complementary screw thread 24 of the connector 2. Using the hexagonal socket 11, he drives the locking member 10 so that the underside 13 of the locking member 10 comes into contact with the connecting member 6.

By continuing to screw the locking member 10 between the branches 25 and 26, the surgeon will exert a force via the locking member 10 on the connecting member 6, and this will push the connecting member 6 until the latter comes to bear against the upper edge 83 of the ring 8.

As locking continues, the ring 8 then slips along the wall 23 of the internal housing 22 until the face 82 of the ring 8 comes into contact with the surface 43 of the head 42 of the anchoring means 4. The surface 43 is itself in contact with the conical section of the wall 23 of the internal housing 22 of the connector 2. The system therefore finds itself in a situation as illustrated in FIG. 2.

During final locking, which will allow the assembly to be immobilized in position, the clamping force imparted by the surgeon via the locking member 10 will allow the ring 8 to be made to slide on the head 42. For that, the face 82 will slide on the surface 43, forcing the ring 8 to open up by deformation until the face 81 of the ring 8 comes into contact over all or part of its surface with the wall 23 of the internal housing 22 of the connector 2. At that moment, the connecting member 6 comes to bear at a point on the spherical surface 44. Thus, the head 42 is immobilized in position, on the one hand, by the ring 8 and, on the other hand, by the connecting member 6 directly. There is thus what is known as three-point contact, two of the points being diametrically opposed points of contact of the edge 83 of the ring 8 with the connecting member 6 and one additional point where the connecting member 6 contacts the surface 44 of the head 42 of the anchoring means 4.

Of course, numerous modifications could be made to the invention without departing from its scope.

Figure 6:
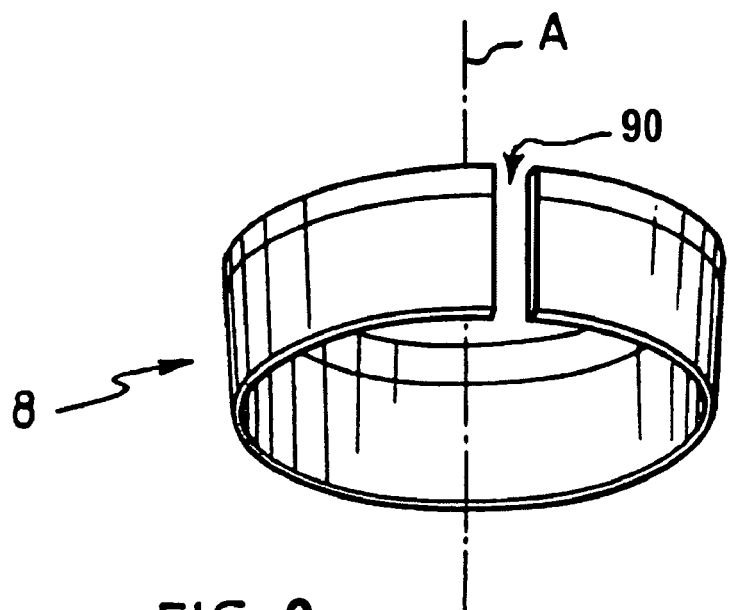
FIG. 6 is a perspective view of an embodiment of the ring as a non-closed annulus.

For example, referring to FIG. 6, the ring 8 could have at least one slot 90. This slot could be arranged in such a way that the ring forms a non-closed annulus.

Figure 7:
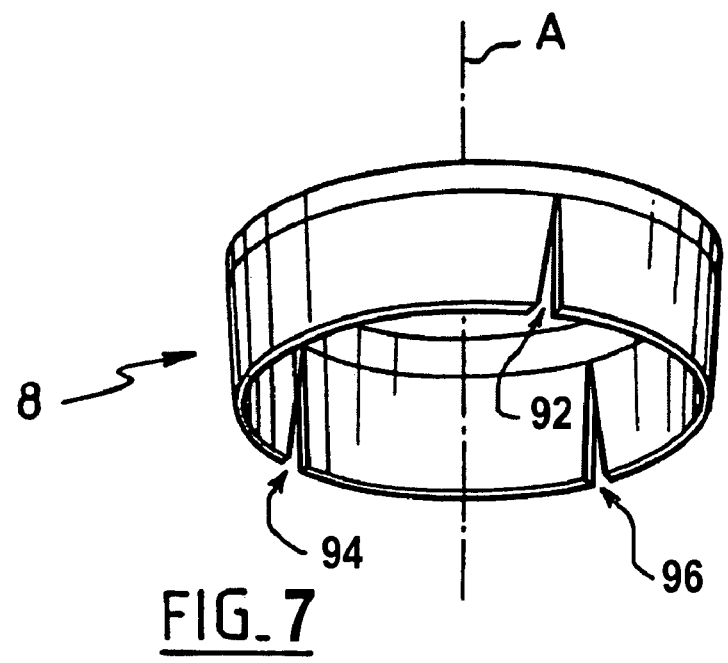
FIG. 7 is a perspective view of an embodiment of the ring with circumferential slots.

Alternatively, referring to FIG. 7, the tapered shape due to the wedge shape of the cross section of the ring, instead of being continuous over its entire circumference, could consist of a number of sectors separated by slots 92, 94 and 96 to form an "umbrella" structure.

These various modifications allow easier deformation of the ring 8. This has the effect of making the ring 8 easier to introduce into the internal housing 22 of the connector 2, on the one hand, and, on the other hand, of making the final locking during use in a surgical operation easier.

The invention claimed is:

1. A spinal osteosynthesis assembly comprising: a connector, a bone anchor received in the connector, a connecting member received in the connector, and a ring, said bone anchor having a polyaxial range of motion having a head that is in contact with said connector, said connecting member and said ring, said connecting member positioned such that it places a downward force against said ring and said bone anchor throughout the polyaxial range of motion of the bone anchor.

2. The assembly according to claim 1, wherein the ring has at least one conical face in cross-section.

3. The assembly according to claim 1, wherein the ring has a first face in contact with the head of the bone anchor.

4. The assembly according to claim 3, wherein the ring has a second face in contact with an inner wall of the connector.

5. The assembly according to claim 4, wherein the first and second faces are coaxial.

6. The assembly according to claim 1, wherein the ring has a upper edge generally perpendicular to an axis of the ring and in contact with the connecting member.

7. The assembly according to claim 6, wherein the ring has a lower edge generally perpendicular to an axis of the ring.

8. The assembly according to claim 1, wherein the ring is arranged to extend between an inner wall of the connector, and the head of the bone anchor when the connecting member bears against the ring and the bone anchor.

9. The assembly according to claim 1, wherein the ring deforms when the connecting member bears against the ring and the bone anchor.

10. The assembly according to claim 1, wherein the ring has a wall thickness which varies according to a height.

11. The assembly according to claim 1, wherein the ring comprises at least one slot distributed about a circumference of the ring.

12. The assembly according to claim 1, wherein the head of the bone anchor comprises a roughly spherical face.

13. The assembly according to claim 12, wherein the head has a first spherical face and a second spherical face which have the same center and different diameters.

14. The assembly according to claim 1, further comprising a locking member that bears against the connecting member.

15. A spinal osteosynthesis assembly comprising:
a connector;
a bone anchor, having a head and a polyaxial range of motion, received in the connector;
a connecting member received in the connector; and a ring being in contact with the head of the bone anchor;

wherein the osteosynthesis assembly is arranged such that the head of the bone anchor is in contact with said connector, said connecting member and said ring, the connecting member is positioned such that it places a downward force against said ring and said bone anchor throughout the polyaxial range of motion of the bone anchor.

16. The assembly according to claim 15, wherein the ring extends between an inner wall of the connector and the bone anchor when the connecting member bears against the ring and the bone anchor.

17. The assembly according to claim 15, wherein said head of said polyaxial screw includes a first spherical face and a second spherical face, the first and second spherical faces having different diameters.

18. A spinal osteosynthesis assembly comprising:
a connector;
a connecting member having a central longitudinal connecting member axis;
a ring; and
a bone anchor having a head and a polyaxial range of motion, and a central longitudinal bone anchor axis;
wherein the bone anchor, the ring, and the connecting member are assembled with the connector and arranged to be tightened against each other;
wherein the head of the bone anchor is in contact with the connecting member, the ring and the connector; and
wherein during tightening of the osteosynthesis assembly, the connecting member is in contact with the ring and the head of the bone anchor when the connecting member axis is substantially perpendicular to the bone anchor axis, and the connecting member is positioned such that it applies a downward force against the ring and the bone anchor throughout the polyaxial range of motion of the bone anchor.

19. The assembly according to claim 18, wherein the ring forms a non-closed annulus.

20. The assembly according to claim 18, wherein said bone anchor is a polyaxial screw, the polyaxial screw has a head comprising a first spherical face and a second spherical face, the first and second spherical faces having the same center and different diameters.

21. A spinal osteosynthesis assembly comprising:
a connector;
a connecting member;
a ring; and
a bone anchor having a head, and a polyaxial range of motion;
wherein the bone anchor, the ring, and the connecting member are assembled with the connector and arranged to be tightened against each other;
wherein the head of the bone anchor is in contact with the connecting member, the ring and the connector; and
wherein the head of the bone anchor contacts the connecting member, the connector, and the ring throughout the polyaxial range of motion of the bone anchor within the connector, and the connecting member is positioned such that it places a downward force against the ring and the bone anchor.

22. A spinal osteosynthesis assembly comprising:
a connector;
a bone anchor received in the connector;
a connecting member received in the connector and having a lowermost portion; and
a ring having a longitudinal axis, said bone anchor having a head that is in contact with said connector, said connecting member and said ring, said connecting member positioned such that its lowermost portion is situated above said ring and said head of said bone anchor as viewed perpendicularly to the longitudinal axis of the ring and such that said connecting member places a downward force against said ring and said head of said bone anchor to lock the assembly, at least a portion of said ring being forced at least partially between the bone anchor and the connector.

23. The assembly of claim 22, wherein said lowermost portion of said connecting member contacts an uppermost portion of said ring.

* * * * *